United States Patent [19]
Youssefyeh

[11] Patent Number: 5,922,359
[45] Date of Patent: Jul. 13, 1999

[54] SKIN TREATMENT COMPOSITIONS COMPRISING UNOXIDIZED NERVE TISSUE

[76] Inventor: Rena T. Youssefyeh, 430 Carroll Close, Tarrytown, N.Y. 10591

[21] Appl. No.: 09/024,892

[22] Filed: Feb. 17, 1998

Related U.S. Application Data

[51] Int. Cl.⁶ .................................................. A61K 35/30
[52] U.S. Cl. ............................................................ 424/570
[58] Field of Search ............................................... 424/570

[56] References Cited

U.S. PATENT DOCUMENTS

| | | | |
|---|---|---|---|
| 2,162,863 | 6/1939 | Ripke et al. | 167/74 |
| 2,717,227 | 9/1955 | Dawson et al. | 167/74 |
| 3,016,334 | 1/1962 | Lewis | 167/91 |
| 4,094,973 | 6/1978 | Robertson | 424/177 |
| 4,375,480 | 3/1983 | Soma | 424/358 |
| 4,474,763 | 10/1984 | Lubowe | 424/177 |
| 4,507,279 | 3/1985 | Okuyama et al. | 424/63 |
| 4,714,615 | 12/1987 | Youssefyeh et al. | 424/570 |
| 5,055,298 | 10/1991 | Kludas | 424/401 |
| 5,431,911 | 7/1995 | Reynolds | 424/401 |
| 5,431,913 | 7/1995 | Phillips | 424/401 |

*Primary Examiner*—Jean C. Witz
*Attorney, Agent, or Firm*—Imre Balogh

[57] ABSTRACT

Topical composition and method for retexturizing skin by peeling the outer layer of dead skin cells, sebum and other impurities, the composition containing unoxidized nerve tissue and a slightly abrasive powdery component in a cosmetically acceptable carrier.

43 Claims, No Drawings

SKIN TREATMENT COMPOSITIONS COMPRISING UNOXIDIZED NERVE TISSUE

BACKGROUND OF THE INVENTION

1. Field of the Invention

This invention relates to a topical skin treatment composition in the form of a cosmetic composition using an improved method for revitalizing and retexturzing the skin, especially by peeling the outer layer of microthin dead skin cells, sebum, and other impurities that are compacted regularly onto the stratum corneum as part of normal metabolism.

2. Reported Development

The layers of skin consist of the epidermis, the dermis and the subcutaneous tissue. The outermost layer, known as the dermis, itself consists of four layers, the stratum corneum, the stratum granulosum, the squamous cell layer, and the basal cell layer. Through a process known as desquamation, the epidermis has the ability to constantly renew itself by shedding the flattened dead skin cells composing the stratum corneum. However, over time this normal metabolic process slows down, calling for skin compositions that effectively peel, exfoliate and remove these dead cells and related impurities, accelerating desquamation that is a part of the natural cell renewal cycle of the skin.

The stratum corneum is the outer coating of the epidermis. It consists of compacted dead cells called keratinocytes that are composed of keratin, a dried out protein. This is the layer of skin that is felt and seen and can be characterized as for example, smooth, soft, oily or flaky. Cells of the basal cell layer take about two to four weeks to migrate upwards through the four epidermal layers until they reach the top layer, the stratum corn. There they are compacted and under optimal circumstances, shed over a period of two to six weeks. Thus, the usual turnover time of the epidermis, namely the time it takes for cells to migrate from the basal cell layer to the point of being shed from the stratum corneum, is about four to eight weeks. However, although the stratum corneum is a multicellular membrane of metabolically active cells, it begins to lose its dynamic ability to constantly renew itself through desquamation with the natural progression of the aging process. Young skin renews its surface layers every 2 to 3 weeks, whereas mature skin may take twice as along to be renewed as compared to young skin. If we accelerate the process by which the rate of dead skin cells in the stratum corneum are being desquamated, then it follows that the rate at which new cells are formed of epidermal tissues, restoring the skin's freshness and youthful appearance.

Periodically, the facial skin of the human body needs a deep cleansing to remove not only dead skin generated by epidermal desquamation, but also the oily particles excreted from oil glands. The second layer of skin or dermis, houses the sebaceous glands. These oil glands continuously excrete and channel oil from the deep dermis to minute openings at the surface of the skin. This natural skin oil, called sebum, has a tendency to solidify over the sebaceous orifice resulting in the formation of hardened plaques. Such plaques contribute to the growth of adverse dermatologic skin conditions such as acne, vulgaris, cysts, white and black heads.

The disease of acne vulgaris is reported to be the singly most common skin disease and affects approximately eighty percent of the teenage population. However, it may persist into the third and fourth decades of life. Acne primarily is a disease of the pilosebaceous system with a multifactorial cause. The pathogenesis includes an androgen dependent increase in sebum production, proliferation of the follicular microflora (principally P. acnes) and alteration in the follicular keratinization. This results in the primary clinical lesions of acnes, namely, the open comedone (blackheads), closed comedone (whiteheads), papules, pustules and nodules. The increased sebum production is responsible for the oily appearance. Currently, therapy is directed towards treatment of the lesions the presence of oil itself is not the cause of acne but is a great psychological problem for the acne patient.

The onset of acne vulgaris is related to adolescence and normal sexual and physical growth. During this rapid linear growth period there is a marked development in the pilosebaceous system which results in sebum production and changes in its composition and physical characteristics. These events are hormonally controlled.

The disease of the pilosebaceous follicle is first detectable by change occurring in the follicular epithelium. The pilosebaceous unit is made up of a hair follicle and a pilosebaceous gland which are connected to the skin surface ducts through which the hair passes. The sebaceous gland produces sebum which is a mixture of fats and waxes that transgress the duct and spread to the skin surface which helps keep the skin soft and moist. The acne lesion develops when the gland and lining begin to work excessively which predominantly occurs during puberty. The glands produce more sebum making the skin oily. The duct normally sheds cells which are carried to the skin surface by the sebum. When acne develops, cells stick together to form a thick layer and plug the duct. More cells and sebum pile up behind this plug which results in the primary lesion of acne, the comedone. If the plug stays below the skin surface, it is called a "closed comedone" or a "whitehead." A comedone which pushes through the surface is referred to as an "open comedone" or "blackhead." This is not due to dirt but due to discoloration or melanin, the dark pigment in normal skin. The whiteheads and blackheads are referred to a "noninflammatory acne lesions." However, the pilosebaceous unit can rupture and become inflamed and these are the pimples, papules, and pustules which are the inflammatory lesions of this disease.

Pilosebaceous units are found all over the body, but they are more predominant on the face, chest, and the back. These are usually the predominant areas which develop acne.

The existence of these plaques in combination with the constant drying of the outermost epidermal cells contributes to the appearance of rough, aged, and unhealthy skin.

There are numerous skin care preparations on the market today which have been designed to promote healthy and youthful-looking skin. Among various preparations include emollients or occlusive agents which moisturize the skin and prevent dryness. Other skin preparations have been formulated to exhibit antiseptic and astringent properties, while still other preparations are used as skin cleansers that attempt to exfoliate the skin. Some of these exfoliating preparations contain abrasive particles such as granulized almond shell, quartz particles and pulverized borax to remove the dead skin cells and hardened plaques. A problem associated with the use of such particles is that they are skin irritants to a degree which many patients find unacceptable Additionally, while some of these abrasive particles may remove some of the foreign matter from the skin, such as make-up and debris, they do not render the skin smooth and soft. They may also remain in the pores of the skin and thus cannot be totally removed. Other preparations incorporate detergent solutions, which have a tendency to cause pronounced drying of the skin without adequately removing foreign matter.

SUMMARY OF THE INVENTION

A cosmetic formulation for cleansing human skin is provided comprising:

a) of from about 12.5 to about 24.5% w/w of an unoxidized nerve tissue;

b) of from about 41 to about 59% w/w of a powdery slightly abrasive material;

c) of from about 16.5 to about 45.5% w/w of a cosmetically or pharmaceutically acceptable vehicle selected from the group consisting of
water,
organic or inorganic liquids,
solid polymeric materials,
surface active agents,
preservatives,
bacteriostats and
fragrances.

The nerve tissue is obtained from mammalian sources, such as bovine, feline, ovine and porcine from nerves per se, spinal cords, and brain. It is heated at a temperature of from about 100° to 165° C. to kill microorganisms but prevented from oxidization.

Alternatively, the nerve tissue is processed to eliminate the presence of microorganism at a temperature of 60 to 70° C. in the presence of a polyol and a surface active agent to prevent oxidation of the nerve tissue.

The powdery, slightly abrasive material used in the present invention comprising particles having an average particle size of from about 0.1 to about 500 μm and is selected from the group consisting of:

a) inorganic powders, such as calcium carbonate;

b) metal soaps such as aluminum stearate; and c) organic powders, such as microcrystalline cellulose.

In one embodiment of the invention, intended for use on oily and/or acne infested skin, fumed silica is used as the inorganic powder which is known for its oil absorptive properties.

In an analogous embodiment of the present invention, again intended for use on oily and/or acne infested skin, a surface active agent is used with the slightly abrasive powders to dissolve and remove the oily exudate of the skin.

In still another embodiment of the present invention intended to help the healing process of skin having inflammatory conditions and other disorders associated with acne, eczema, aging skin and the like, pharmaceutically active agents are incorporated, such as anti-inflammatory analgesics, anesthetics, antibiotics, antivirals, antiseptics, vitamins and antifungals.

The composition of the present invention is in the form of creams, gels, lotions, suspensions, pastes, and foams known in the art. In accordance with the requirements in these forms, emollients, fragrances, emulsifiers, thickening agents, solvents, preservatives and buffering agents are incorporated for reasons known in the art. The presence or absence of some of these ingredients are directed by the intended use of the compositions. For example, for use on dry or aging skin the emollients and lubricants will predominate, for oily, acne infested skin the lack of emollients and lubricants is important, while for damaged skin the incorporation of active pharmaceutical and therapeutic agents are required to help the healing process.

The compositions of the present invention are particularly adapted for topical application in effective amounts directly to the facial and neck area. In a typical application procedure, the treatment area of the skin is steamed for 3 to 5 minutes. The composition is then sparsely or liberally applied to the throat and face by hand. Care should be exercised during application of the facial composition to avoid contact with the eyes. The composition is massaged lightly onto the treatment area for a time sufficient to cleanse and/or exfoliate the same, for example, 1 to 2 minutes. The resulting peeled or exfoliated dead skin cells and material can be removed completely by rinsing the skin with warm water and thereafter patted dry. Revitalization of the treated skin occurs, with improvement of skin texture and clarity resulting from the peeling of dead skin and grime These results are noticeable immediately, with subjects experiencing a smoother appearance and "rosy glow" to their complexions.

DETAILED DESCRIPTION OF THE INVENTION

The present invention provides compositions and methods for peeling dry dead skin, cleansing the skin and treating acne and other disorders of the skin by applying the composition onto the desired area and rinsing them off with water.

The care of the composition comprises an admixture of unoxidized nerve tissue and a slightly abrasive particulate powder. Other ingredients incorporating the admixture provide advantageous properties to the admixture by which specific results may be obtained, such as removing oily exudate and reducing the presence of acne.

The invention will now be described in detail.

The Nerve Tissue

The nerve tissue used in the preset invention is of mammalian sources, such as bovine, feline, ovine and porcine. Best results are obtained with bovine nerve tissue. The nerve tissue is obtained from nerves per se, spinal cords and brain; spinal cords are preferred.

In preparing the nerve tissue of the present invention, raw materials are obtained from commercial sources. After thorough washing with deionized water the lamina is removed from the spinal cord, washed again with deionized water, placed onto a smooth plastic surface and cut into 1 to 3 cm pieces. The pieces are placed into an industrial, steam jacketed pressure container containing a motorized stirrer and cover to exclude air so that the tissues remain oxidized. Purified water is added and is heated at a temperature of from about 100° to 165° C. for about 15 to 30 minutes while the content is being stirred with the motorized stirrer to obtain a liquid mixture. The heating process insures that the presence of microorganism is eliminated.

When inorganic powders are used as the slight abrasive materials, such as calcium carbonate, the powders are added to the pressure container and the mixture is stirred for another 15 to 30 minutes while continuing heating at about 100° to 165° C. At the end of the heating process the pressure container, still covered, is cooled to ambient temperature. The pH of the cooled mixture is adjusted to about 5 to 7, and preferably to 6.6 to 6.8 with an acid, such as citric, fumanic, glycolic, hydrochloric, maleic, malonic, salicylic, succinic and sulfamic acid. The pH adjusted material is ready to be combined with a cosmetically acceptable vehicle or other desirable excipients.

Alternatively, a lower temperature heating process may also be used, which also insures the elimination of microorganisms in the nerve tissue material. The process comprises:

heating and simultaneously agitating, such as stirring a mixture of nerve tissue and deionized water in a pressure container at about 60° to 70° C. for about 10 to 20 hours to effect pasteurization thereof in the presence of; 25% to 50% w/v of a polyol selected from the group consisting of sucrose, maltose, lactose, glucose, mannose, and galactose; and 0.01% to 0.5% w/v of a surface active agent selected from the group consisting of polyoxyethylene sorbitan mono- and tri-esters, sodium cholate, sodium taurocholate, sodium deoxycholate, and sodium glycocholate.

After the heating process, the mixture is cooled to ambient temperature and the additives are filtered off. The pure nerve tissue is then formulated into cosmetic formulations.

Other polyols may be substituted for the disaccharide sucrose, such as: other disaccharides, such as maltose and lactose; monosaccharides, such as glucose galactose and mannose; certain polyhydric alcohols, such as glycerol; and certain polymers such as polyethylene glycol.

Other surface active agents useful include nonionic agents such as alkyl phenyl polyoxyethylenes (such as Triton® and Nonidet®; anionic agents such as the bile salts (sodium taurocholate, sodium cholate, sodium deoxycholate and sodium glycocholate); cationic agents such as benzalkonium chloride; and polyhydric alcohols with surface active properties such as the high molecular weight copolymers of propylene glycol and propylene oxide sold under the trade names of Pluronic® F-38 and Pluronic® F-68.

Still further, to insure against the presence of microorganism, the mixture of nerve tissue and the powdery abrasive material may be freeze-dried in a finely divided form, which is then reconstituted by water prior to use.

Appropriate proportions of the unoxidized nerve tissue and the powdery abrasive material are admixed and pulverized to the desired particle size and placed into small, gas impermeable open bags, such as made from polyvinylidene chloride. The mixture preferably contains a preservative and a fragrance.

After filling, the open bags are loaded into a drying chamber and placed directly onto the refrigerated shelves which were pre-chilled to 4° C. Thermocouples are placed inside a number of the bags to monitor the temperature of the mixture during the lyophilization process. The bags are then allowed to equilibrate to the temperature of the shelves (4° C.) before lowering the shelves' temperature to −40° C. Once reaching −40° C., the bags are kept at this temperature for about 6 hours to allow complete freezing of the mixture. After this time period the condenser coils are chilled to −80° C. and the vacuum pump is turned on to evacuate the condenser chamber followed by the process of primary and secondary drying. In the primary drying process, the main valve between the condenser and the drying chamber is opened and the drying chamber is evacuated to a pressure of about 100 microns with a nitrogen gas bleed. Upon reaching a pressure of 100 microns, the shelf temperature is raised to −20° C. to start the sublimation process. This portion of the lyophilization cycle requires about 10 to 18 hours. The primary drying process is complete when all of the ice disappears from the frozen matrix and the thermocouple temperature has reached −20° C. In the secondary drying process, the temperature is raised from −20° C. to +25° C. to remove all the ice that was not removed during the lyophilization process. This removal required approximately 4 to 8 hours.

The open bags then are sealed, such as by heat sealing or other means and stored. When intended to use, the bag is cut open, the content is transferred to an appropriate small container and reconstituted with water. Alternatively, the powdery mixture may be applied directly to the skin without reconstitution with water.

Still further, to insure against the presence of microorganisms, the mixture of nerve tissue and the powdery material comminuted to the desired particle size and admixed with a preservative and fragrance may be sterilized in sealed bags or other containers by other well known means, such as irradiation or by treatment with ozone gas.

Cosmetically Acceptable Abrasive Particulates

The present invention utilizes cosmetically acceptable particulates incorporated in the formulation for imparting slight abrasive properties when the formulations are applied to skin. The abrasive particles help in separating and removing the dead skin cells which compose the stratum corneum The abrasive particles include:

a) inorganic powders, such as calcium carbonate, acetate, formate, gluconate, lactate, oxalate, phosphate or stannate; magnesium carbonate; zinc carbonate; magnesium aluminum silicate; silica; zinc aluminum silicate; talc; kaolin; cericite; mica; vermiculite; diatomaceous earth; calcium silicate; barium silicate; barium sulfate; hydroxyapatite; zeolite; and boran nitride;

b) metal soaps, such as aluminum stearate, magnesium stearate and zinc stearate; and c) organic powders, such as nylon, polyethylene, polystyrene, polytetrafluoroethylene, epoxy, acrylic, microcrystalline cellulose, phenol resin, vinyl resin, vinylidene resin, polyurethane resin, natural rubber, synthetic rubber, chitosan, fibroin keratin, polyvinylpyrrolidone, polyvinyl alcohol and ethylene oxide polymers;

sulfated polysaccharides, such as sugars, cellulose, starch and glycogen;

sulfated esters of polysaccharides, such as, carageenan, furcellaren, laminaran sulfate, galactan sulfate, chondroitin sulfate;

carboxylated polysaccharides, such as pectin., algin and gum karaya;

cellulose derivatives, such as sodium ethylcellulose sulfate, sodium cellulose acetate sulfate and sodium carboxymethyl cellulose.

The metal soaps (b) and organic powders are preferably coated with magnesium aluminometasilicate.

The average particle size of the inorganic and organic powders and metal soaps is in the range of from about 0.21 to about 500 μm, preferably 50 to 300, and most preferably about 100 to 200 μm.

The coating on the metal soaps and organic powders is from about 5 to about 90 parts per weight of the total weight of the composite.

The form of the powders and soaps may be spherical, plate, granule or needle, the spherical form is preferred.

In an embodiment of the present invention intended for use on oily skin, such as acne infested skin, fumed silica is used as the slightly abrasive material since it possesses excellent oil-absorptive properties as disclosed in U.S. Pat. No. 4,536,399 which is incorporated herein by reference.

Fumed silica is a synthetic, amorphous, colloidal silicon dioxide. It is produced by the vapor hydrolysis of chlorosilanes, such as silicon tetrachloride, in a hydrogen-oxygen flame:

$$SiCl_4+2H_2O+O_2 1800° C. SiO_2+4HCl$$

In the combustion process, molten spheres of amorphous silica are formed. These particles are produced in various sizes, ranging from 7 to 21 nanometers in diameter yielding a surface area of 400 to 130 square per gram. These primary particles collide and fuse to form branched, threedimensional, chain-lie aggregates. Further agglomeration takes place below the fusion temperature, until the size of the agglomerates ranges from approximately 0.5 to 10 microns.

Fumed silica meets all of the requirements for "Colloidal Silica Dioxide" as described in the USP-National Formulary.

A preferred fumed silica is CB-O-SIL.

CAB-O-SIL fumed silica is pure commercially available amorphous silica. It is at least 99.8 percent by weight silicon dioxide on an ignited weight basis. Typical levels of trace metallic impurities are show below:

Typical Analysis of CAB-O-SIL
for Trace Metallic Contaminants

| Element | ppm | Element | ppm | Element | ppm |
|---------|-----|---------|-----|---------|-----|
| Ag | 0.1 | Cr | 1 | P | 3 |
| Al | 2 | Cu | 0.5 | Pb | 0.1 |
| As | 0.2 | Fe | 2 | Sb | 0.1 |
| B | 2 | Hg | 0.1 | Se | 0.1 |
| Ba | 1 | Li | 0.1 | Sn | 1 |
| Be | 0.5 | Mg | 0.5 | Ti | 2 |
| Bi | 2 | Mn | 0.5 | V | 2 |
| Ca | 2 | Mo | 2 | Zn | 1 |
| Cd | 0.1 | Na | 5 | Zr | 5 |
| Co | 0.5 | Ni | 2 | | |

Many agents were investigated to determine their oil absorption potential. These agents included kaolin, aluminum hydroxide, precipitated silica, and fumed silica. Fumed silica was found to be substantially superior to the other agents. The property of the ability to absorb skin oil is determined by using the ASTM method for oil absorption. Squalene, the principal oil found in sebum, is used as the oil to be absorbed. See Table I below for the results.

TABLE I

OIL ABSORPTION CAPACITY OF VARIOUS INGREDIENTS
AS DETERMINED BY ASTM RUBOUT METHOD*

| | |
|---|---|
| Bentonite | 50.1 g |
| Aluminum Hydroxide | 52.7 g |
| Georgia Kaolin Bentonite | 57.0 g |
| Microfine Bentonite | 51.0 g |
| Syloid 244 Silica Precipitated | 275 g |
| Silica Fumed | 428 g |

*Results expressed as grams of oil absorbed per 100 grams of sample.

In another embodiment of the present invention intended for use on extremely oily skin, and anionic surface active agent is admixed with the slightly abrasive particulates to help dissolve and remove the oily exudate of the skin.

The anionic surfactant component is selected from the group consisting of sodium and potassium salts of $C_{12}$–$C_{18}$ saturated monocarboxylic acids, a water-soluble, non-soap, anionic detergent selected form the group consisting of sodium or potassium salts of $C_8$–$C_{18}$ acyl isethionates, $C_8$–$C_{18}$ alkyl sulfates, $C_{10}$–$C_{20}$ alkyl sulfonates, $C_8$–$C_{18}$ monoglyceride sulfonates $C_8$–$C_{16}$ alkylbenzene sulfonates and $C_8$–$C_{18}$ alkyl polyethenoxy ether sulfates containing one to twelve ethenoxy groups in the molecule and mixtures thereof and mixtures of said monocarboxylic acid salt with said non-soap detergent in specified ratios. Suitable saturated monocarboxylic acids which may be neutralized to form the sodium or potassium salt include lauric acid, myristic acid, palmitic acid, pentadecanoic acid, heptadecanoic acid, stearic acid and mixtures thereof. The acids containing an even number of carbon atoms can be obtained by hydrolysis of hydrogenated natural fats or oils, e.g., coconut oil, palm kernel oil and beef tallow, as well as from synthetic sources; whereas the acids containing an odd number of carbon atoms are available from synthetic sources. The sodium and potassium salts of the saturated monocarboxylic acids are obtained by neutralizing the monocarboxylic acid with an alkaline sodium or potassium salt such as sodium hydroxide, potassium hydroxide, potassium carbonate or sodium carbonate in a known manner. The preferred monocarboxylic salts are the potassium salts and such preferred potassium salts include commercial potassium stearate, commercial potassium palmitate and potassium salts of commercial mixtures of palmitic acid and stearic acid, with the commercial potassium stearate containing 65% by weight of potassium stearate being most preferred.

As an alternate to the sodium and potassium salts of $C_{12}$–$C_{18}$ saturated monocarboxylic acids, the anionic surfactant component may be a water-soluble, non soap, anionic or potassium salt of a $C_8$–$C_{18}$ alkyl sulfate or alkyl(polyethenoxy)ether sulfate, a $C_{10}$–$C_{16}$ alkylbenzene sulfonate, a $C_{10}$–$C_{20}$ alkyl sulfonate, a $C_8$–$C_{18}$ alkyl monoglyceride sulfate or a $C_8$–$C_{18}$ acyl isethionate. Suitable alkyl sulfates include sodium lauryl sulfate, potassium myristyl sulfate and sodium $C_{10}$–$C_{16}$ alkyl polyethenoxy sulfates containing from 1–12 ethenoxy groups in the molecule. Satisfactory alkylbenzene sulfonates may contain either a branched chain or straight chain alkyl group, with the straight chain alkyl being preferred for biodegradability, and suitable alkylbenzene sulfonates include sodium dodecylbenzene sulfonate, potassium dodecylbenzene sulfonate, sodium decylbenzene and sodium pentadecylbenzene sulfonate. Suitable alkane sulfonates include sodium $C_{13}$–$C_{17}$ alkane sulfonate, sodium tetradecyl sulfonate and sodium pentadecyl sulfonate. Among the suitable $C_8$–$C_{18}$ alkyl monoglyceride sulfates are the sodium and potassium salt wherein the alkyl portion is derived form coconut oil, e.g., sodium coconut monoglyceride sulfate. Satisfactory acyl isethionates correspond to the formula $RCOOCH_2CH_2SO_3M$ wherein the RCO is an acyl radical of 8 to 18 carbon atoms and M is sodium or potassium. Satisfactory materials include the salts of the fatty acid mixture derived from coconut oil in which a major proportion of $C_{12}$ and $C_{14}$ fatty acids are present. Preferred non-soap detergents are the alkyl ethenoxy sulfates, monoglyceride sulfates and acyl isethionates, with said isethionates being most preferred.

In addition, the anionic surfactant component may be a mixture of the foregoing sodium and potassium slats of $C_{12}$–$C_{18}$ saturated monocarboxylic acids with said non-soap anionic detergent slat in a weight ratio of soap to anionic non-soap detergent of about 18:1 to about 2.5:1, preferably 9:1 to about 2.5:1, most preferably about 5:1. It is preferred that the surfactant component be a mixture of the preferred potassium soap and a water-soluble, non-soap, anionic detergent.

The proportion of the anionic surfactant material in the composition will be from about 8% to 38%, preferably about 12% to 15% by weight.

In still another embodiment of the present invention, ingredients which contribute to the healing process of skin having inflammatory conditions and other disorders may be used. Such conditions and disorders include: allergic contact dermatitis, psoriasis, eczematous or atopic dermatitis, acne vulgaris, comedones, polymorphs, nodulokystic acne, conglobata, senile acne, secondary acne such as solar acne, medicinal acne, irritant contact dermatitis or professional acne; other types of keratinization disorders, for example, ichthyoses, ichthyosiform conditions, Darier malady, palmoplantary keratodermies, leucoplasies and leucoplasiform conditions and lichen; other dermatologic disorders such as cutaneous T-cell lymphoma, blistery dermatoses and collagen maladies; and aging of the skin.

Pharmaceutical and therapeutic actives that can be incorporated into the formulations of the present invention include the following:

Anti-inflammatory agents such as salicylic acid, salicylate esters and salts, acetylsalicylic acid, diflunisal, acetaminophen, phenylbutazone, oxyphenbutazone, sulfinpyrazone, indomethacn, sulindac, fenoprofen, flurbiprofen, ibuprofen, ketoprofen, naproxen, mefenamic acid, floctafenine, tolmetin, zomepirac, diclofenac and piroxicam and the like.

Local anesthetics such as cocaine, benzocaine, tetracaine, lidocaine, bupivacaine, their hydrochloride salts, and the like.

Antibiotic agents such as penicillins, cephalosporins, vancomycin, bacitracin, cycloserine, polymyxins, colistin, nystatin, amphoteriin B, mupirocim, tetracyclines, chloramphenicol, erythromycin, neomycin, streptomycin, kanamyin, gentamicin, tobramycin, amikacin, netilricin, spectinomycin, clindamycin, rifampin, nalidixic acid, flucytosine, griseofulvin and the like.

Sulfanilamide antibacterial agents such as sulfanilamide, sulfacetamide, sulfadiazine, sulfisoxazole, sulfamethoxazole, trimethoprin, pyrimethamine, and the like.

Antiviral agents such as vidarabine, acyclovir, ribavirin, amantadine, hydrochloride, rimantadine, idoxyuridine, interferons, and the like.

Antiseptic agents such as acridine dyes, alcohols, bronopol, chlorhexidine, phenols, hexachlorophene, organic mercurials, organic peroxides, i.e. benzoyl peroxide, quartemary ammonium compounds, and the like.

Vitamin and vitamin derivatives such as Vitamin A, retinol, retinoic acid (both cis and trans), alpha-tocopherol (Vitamin E), 7-dehydrocholesterol (Vitamin D), Vitamin K, thiamine, riboflavin, niacin, pyridoxine, biotin, pantothenic acid, ascorbic acid, choline, inositol, and the like.

Anti-inflammatory corticosteroids such as progesterone, hydrocortisone, prednisone, fludrocortisone, triamcinolone, dexamethasone, betamethasone, fluocinolone, and the like.

Anti-fungal agents such as miconazole, tolnaftate, naftifine hydrochloride, undecylic acid and its salts, and other heterocyclic compounds including morpholine, imidazoles and derivatives thereof.

Pharmaceutically/Cosmetically Acceptable Carriers

The nerve tissue and the slightly abrasive powder combination of the present invention is formulated as creams, gels, emulsions, lotions, suspensions, pastes, foams, or any other formulations suitable for topical administration.

To formulate a composition, the weight fraction of the nerve tissue and the slightly abrasive powder is dissolved, suspended, dispersed or otherwise mixed in a selected vehicle. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream [USP], and hydrophilic ointment [USP].

The choice of an acceptable vehicle is largely determined by the mode of application and tissue to be treated. Suitable pharmaceutically and dermatologically acceptable vehicles for topical application include those suited for use and include lotions, creams, solutions, gels, and the like. Generally, the vehicle is either organic in nature or an aqueous emulsion. The vehicle may include pharmaceutically-acceptable emollients, skin penetration enhancers, coloring agents, fragrances, emulsifiers, thickening agents, and solvents.

The lotions contain from 3% to 10% w/w of an emollient and the balance water, a suitable buffer, a $C_2$ or $C_3$ alcohol, or a mixture of water of the buffer and the alcohol. Any emollients known to those of skill in the art as suitable for application to human skin may be used. These include, but are not limited to, the following:

(a) Hydrocarbon oils and waxes, including mineral oil, petrolatum, paraffin, ceresin, ozokerite, microcrystalline wax, polyethylene, and perhydrosqualene.

(b) Silicone oils, including dimethylpolysiloxanes, methylphenylpolysiloxanes, water-soluble and alcohol-soluble silicone-glycol copolymers.

(c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil and soybean oil.

(d) Acetoglyceride esters, such as acetylated monoglycerides.

(e) Ethoxylated glycerides, such as ethoxylated glyceryl monostearate.

(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate diisopropyl adipate, diisohexyl adipate, dihexyldecyl adipate, diisopropyl sebacate, lauryl lactate, myristyl lactate, and cetyl lactate.

(g) Alkenyl esters of fatty acids having 10 to 20 carbon atoms. Examples thereof include, but are not limited to, oleyl myristate, oleyl stearate, and oleyl oleate.

(h) Fatty acids having 9 to 22 carbon atoms. Suitable examples include, but are not limited to pelargonic, lauric, myristic, palmitic, stearic, isostearic, hydroxystearic, oleic, linoleic, ricinoleic, arachidonic, behenic, and erucic acids.

(i) Fatty alcohols having 10 to 20 carbon atoms, such as but not limited to, lauryl, myristyl, cetyl, hexadecyl, stearyl, isostearyl, hydroxystearyl, oleyl, ricinoleyl, behenyl, erucyl, and 2-octyl dodecyl alcohols.

(j) Fatty alcohol ethers, including, but not limited to, ethoxylated fatty alcohols of 10 to 20 carbon atoms, such as, but are not limited to, the lauryl cetyl, stearyl, isostearyl, oleyl, and cholesterol alcohols having attached thereto from 1 to 50 ethylene oxide groups or 1 to 50 propylene oxide groups or mixtures thereof.

(k) Ether-esters, such as fatty acid esters of ethoxylated fatty alcohols.

(l) Lanolin and derivatives, including but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

(m) Polyhydric alcohols and polyether derivatives, including, but not limited to, propylene glycol, dipropylene glycol, polypropylene glycol [M.W. 2000–4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200–6000], methoxy polyethylene glycols 350, 550, 750, 2000, 5000, poly)ethylene oxide) homopolymers [M.W. 100,000–5,000,000], polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol and polyoxypropylene derivatives of trimethylolpropane.

(n) Polyhydric alcohol esters, including, but not limited to, ethylene glycol mono- and di-fatty acid esters, diethylene glycol mono- and di-fatty acid esters, polyethylene glycol [M.W. 200–6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

(o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

(p) Vegetable waxes, including, but not limited to, carnauba and candelilla waxes.

(q) Phospholipids, such as lecithin and derivatives.

(r) Sterols, including, but not limited to, cholesterol and cholesterol fatty acid esters.

(s) Amides, such as fatty acid amides, ethoxylated fatty acid amides, and solid fatty acid alkanolamides.

The lotions further preferably contain from 2% w/w to 5% w/w, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxides, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g. sodium, potassium and triethanolamine soaps, wherein the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably, the compound is dissolved, suspended or otherwise uniformly dispersed in the mixture.

Other conventional components of such lotions may be included. One such additive is a thickening agent at a level from 1% to 5% w/w of the composition. Examples of suitable thickening agents include, but are not limited to: cross-linked carboxypolymethylene polymers, ethyl cellulose, polyethylene glycols, gum, tragacanth, gum kharaya, xanthan gums and bentonite, hydroxyethyl cellulose, and hydroxypropyl cellulose.

Creams

The creams contain from 3% to 10%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included in the composition at a level from 2% to 5%.

Suspensions

The vehicle for suspensions is water, a suitable organic solvent, a buffer or mixtures thereof. Suitable organic materials useful as the solvent or a part of a solvent system are as follows: propylene glycol, polyethylene glycol [M.W. 200–600], polypropylene glycol [M.W. 425–2025], glycerine, sorbitol esters, 1,2,6-hexanetriol, ethanol, isopropanol, diethyl tartrate, butanediol and mixtures thereof. Such solvent systems can also contain water.

Suspensions used for topical application can include any of the following components: a sterile diluent, such as water, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid [EDTA]; buffers, such as acetates, citrates and phosphates; and agents for the adjustment of tonicity such as sodium chloride or dextrose. Suitable carriers may include physiological saline or phosphate buffered saline [PBS], and the suspensions may contain thickening agents, such as glucose, polyethylene glycol, and polypropylene glycol and mixtures thereof.

Formulations

Formulation examples of the present invention follows.

| Ingredients | % by Weight |
| --- | --- |
| Example 1, Generic Core Formula | |
| Unoxidized nerve tissue | 12.5–24.5 |
| Powdery abrasive material | 41.0–59.0 |
| Vehicle | 16.5–45.5 |
| Purified water | 5.0–42.0 |
| Acid or buffer | 0.2–530 |
| Bacteriostat | 0.01–2.1 |
| Fragrance | 0.005–0.08 |
| Example 2 | |
| Calcium carbonate | 50.0 |
| Unoxidized nerve tissue | 16.0 |
| Acid or buffer | 0.2 |

-continued

| Ingredients | % by Weight |
|---|---|
| Bacteriostat | 0.2 |
| Fragrance | 0.01 |
| Water q.s. | 100.00 |

Example 3

| Ingredients | % by Weight |
|---|---|
| Calcium carbonate | 55.0 |
| Unoxidized nerve tissue | 20.0 |
| Acid or buffer | 0.4 |
| Bacteriostat | 0.8 |
| Fragrance | 0.06 |
| Water q.s. | 100.00 |

Example 4

| Ingredients | % by Weight |
|---|---|
| Calcium carbonate | 51.72 |
| Unoxidized nerve tissue | 17.24 |
| Acetic acid | 0.28 |
| Methyl paraben | 0.19 |
| Propyl paraben | 0.19 |
| Bromopal | 0.04 |
| Fragrance (mint or flower essence) | 0.04 |
| Water q.s. | 100.00 |

Example 5

| Ingredients | % by Weight |
|---|---|
| Fumed silica | 50.0 |
| Unoxidized nerve tissue | 18.5 |
| Citric acid | 0.30 |
| Methyl paraben | 0.20 |
| Propyl paraben | 0.50 |
| Bromopal | 0.030 |
| Fragrance (synthetic) | 0.020 |
| Water q.s. | 100.00 |

Example 6

| Ingredients | % by Weight |
|---|---|
| Polystyrene | 46.5 |
| Unoxidized nerve tissue | 15.5 |
| Adipic acid | 0.3 |
| Methyl paraben | 0.2 |
| Propyl paraben | 0.2 |
| Bromopal | 0.05 |
| Fragrance (flower essence) | 0.05 |
| Water q.s. | 100.00 |

Example 7

| Ingredients | % by Weight |
|---|---|
| Magnesium aluminum silicate | 42.0 |
| Unoxidized nerve tissue | 13.0 |
| Salicylic acid | 0.7 |
| Lanolin alcohol | 0.10 |
| Emulsifying wax NF | 7.00 |
| PEG-20 glycerides | 3.0 |
| Petrolatum | 34.2 |

Example 8

| Ingredients | % by Weight |
|---|---|
| Silica | 41.0 |
| Unoxidized nerve tissue | 19.0 |
| Benzyl alcohol | 3.5 |
| Propylene glycol | 9.0 |
| Stearyl alcohol | 90 |
| Poloxamer | 7.0 |
| Water q.s. | 100.00 |
| Buffer to pH | 7.0 |

Example 9

| Ingredients | % by Weight |
|---|---|
| Zinc aluminum silicate | 41.0 |
| Unoxidized nerve tissue | 12.5 |
| Ethanol | 7.0 |
| Hydroxyethyl cellulose | 3.0 |
| Water q.s. | 100.00 |
| Buffer to pH | 6.8 |

Example 10

| Ingredients | % by Weight |
|---|---|
| Calcium oxalate | 42.0 |
| Unoxidized nerve tissue | 13.0 |
| Potassium stearate | 7.0 |
| Potassium myristyl sulfate | 6.0 |
| Fumaric acid | 0.2 |
| Water q.s. | 100.00 |

Example 11

| Ingredients | % by Weight |
|---|---|
| Aluminum stearate | 49.0 |
| Unoxidized nerve tissue | 13.5 |
| Vitamin E | 2.0 |
| Sulfamic acid | 0.2 |
| Ethyl alcohol | 9.0 |
| Water q.s. | 100.00 |
| Buffer to pH | 7.0 |

Example 12

| Ingredients | % by Weight |
|---|---|
| Barium silicate | 41.0 |
| Unoxidized nerve tissue | 12.5 |
| Guar gum | 20.0 |
| Calcium lactate | 0.2 |
| Benzyl alcohol | 0.5 |
| Methyl paraben | 0.2 |
| Water q.s. | 100.00 |

The present invention in a cream form called "improved product" was comparatively tested against the product in a cream form called "original product" disclosed in U.S. Pat. No. 4,714,615 as described hereunder.

Our approach used for comparison of the original product and the improved product involved clearly defined experimental analysis of a group study. The 100 panelists represented a cross section of women ages 28 to 55 and men ages 30 to 50. Since our objective was to secure as much information as possible in the shortest time, we opted for a test in which each panelist would have an opportunity to preliminarily practice the evaluation of a placebo product in a central location, under supervision. In this way the panelists could inspect the placebo product, apply it, and evaluate appearance and texture, each panelist fully comprehending the nature of what was expected of them.

An interviewer called the panelists 1 week prior to the study, to determine eligibility and interest on the part of the panelist. Those panelists qualifying according to expressed interest in the product, and according to age requirements, became members of the panel. Thus, the panelists participated in one initial test session at a central location under supervision. Subsequently, the panelists received both products for home use, and corresponding questionnaires requiring the evaluation of each product pursuant to each application. Finally, the panelists returned to the central location 40 days later, with completed questionnaires profiling each product. To secure the appropriate panel of 100 respondents, the recruiter developed a panel of 108, recognizing that some people would not show up for the test sessions.

The study provided an opportunity for the panelists to perform the task of evaluating the original product and the improved product as intended, and in a relaxed way at home, for appropriateness and for different sensory dimensions. Each panelist had to evaluate the original product and the improved product on a variety of attributes.

To obtain the best data, the panelists rated the product in terms of the following attributes/conditions:

(1) smoothness of product; How grainy did the product feel when applying? Was it thick enough? Was it creamy enough?

(2) existence of any post-use residue;
(3) appropriateness of product fragrance; Was the odor too strong? Too weak?
(4) ease of application; How easy was the product to apply?
(5) immediacy of effect; How well did the product clean the skin? How fresh did the skin feel after application?
(6) general appeal of product appearance; Was the product found appealing/attractive? and
7) performance of product; How appropriate was the product overall? Did the product live up to the panelist's expectations? How dry did the skin feel after application?

The panelists profiled their conclusions using the same scale and attributes for each product and the same questionnaires. The scale consisted of the following ratings: strong preference for improved product, preference for improved product, no preference, preference for original product, strong preference for original product. Each product was packaged so that they could be introduced on a "blind" basis. The original product was to be applied repeatedly each week for four weeks on the left side of the face, and the improved product was to be applied repeatedly each week for four weeks on the right side of the face. The specific test followed the previous approach outlined above. The sequence of steps for the test were the following:

1. Panelists recruited randomly by telephone and invited to participate.
2. Panelists oriented in scaling in introductory exercise.
3. Panelists read a setup concept about the category.
4. Panelists apply a training product, for orientation purposes.
5. Panelists rate the training product on the attributes.
6. Panelists ratings checked for consistency and comprehension.
7. Panelists receive both products, for home use, and questionnaires.
8. Panelists return 40 days later, with completed questionnaires profiling each of the two products.

In differentiating the products, the following conclusions were drawn from 100 completed questionnaires:

90% of the panelists strongly preferred the new product's smoothness of texture over the original product. The remaining 10% of panelists preferred the improved product's texture over the original product.

100% of the panelists rendered the improved product a strong preference rating with respect to any residual effect existing on the skin after use. The reason had to do largely with immediate and superior performance of the improved product, which unlike the original product, leaves no residue on the skin post use.

With respect to the panelists' feelings about each product's smell, 94% strongly preferred the improved product's more natural odor, which panelists considered more appealing than the original product's odor, and 4% indicated a preference for the improved product and 2% felt impartial.

96% of panelists found the improved product much easier to apply, rating the new product strongly preferable and the remaining 4% of panelists found the new product preferable in comparison to the original product in rendering the immediate peeling of dead skin and impurities.

With respect to the comparison of product quality, 98% of panelists selected the improved product as strongly preferable to the original product in leaving skin more clean, refreshed and rejuvenated. 1 panelist indicated the improved product as preferable to the old product, and 1 panelist could not distinguish the benefit of either product over the other in this category.

97% of panelists concluded that the improved product was strongly preferable to the old product in the determination of a general appeal of each product's appearance, thus confirming the overall appropriateness of the improved product's attributes and the overwhelming preference for the new product's attributes over the original product's attributes. 3% of panelists indicated a preference for the improved product.

92% of panelists strongly preferred the improved product to the old product, and the remaining 8% of panelists preferred the improved product over the original, concluding the performance of the improved product as superior to that of the old product.

The results determined from seven categories of questions set forth to distinguish and compare the qualities of both the improved product and the original product reveal an overwhelming preference for the improved product with respect to overall product performance and general sensory attributes.

This invention has been described in detail with particular reference to certain preferred embodiments thereof, but it will be understood that variations and modifications can be effected within the spirit and scope of the invention.

What is claimed is:

1. A topical skin treatment composition comprising:
   a) of from about 12.5 to about 24.5% w/w of unoxidized nerve tissue; and
   b) of from about 41 to about 59% w/w of powdery, slightly abrasive material in finely divided from having an average particle size of from about 0.1 to about 500 μm;
   said unoxidized nerve tissue and said slightly abrasive material admixed together and lyophilized,
   wherein said unoxidized nerve tissue is obtained by heating nerve tissue obtained from the spinal cords and brains of bovine, feline, ovine or porcine sources at a temperature of from about 100° to 165° C. with the exclusion of air.

2. The topical skin treatment composition of claim 1 wherein said unoxidized nerve tissue is obtained by heating nerve tissue obtained from the spinal cords and brains of bovine, feline, ovine or porcine sources at a temperature of from about 60° to about 70° C. for about 10 to 20 hours in the presence of:
   water;
   20 to 50% w/w of a polyol selected from the group consisting of sucrose, maltose, lactose, glucose, mannose and galactose; and
   0.01 to 0.5% w/w of a surface active agent selected from the group consisting of polyoxethylene sorbitan mono- and tri-esters, sodium cholate, sodium taurocholate, sodium deoxycholate and sodium glycocholate.

3. The topical skin treatment composition of claim 1 wherein said unoxidized nerve tissue is obtained by heating nerve tissue obtained from the spinal cords and brains of bovine, feline, ovine or porcine sources at a temperature of from about 60° to about 70° C. for about 10 to 20 hours in the presence of:
   water;
   20 to 50% w/w of a polyol selected from the group consisting of glycerol and polyethylene glycol; and
   0.01 to 0.5% w/w of a surface active agent selected from the group consisting of alkyl phenyl polyoxyethylenes, bile salts and benzalkonium chloride.

4. The topical skin treatment composition of claim 1 wherein said unoxidized nerve tissue is obtained by irradiating nerve tissue obtained from the spinal cords and brains of bovine, feline, ovine or porcine sources.

5. The topical skin treatment composition of claim 1 wherein said unoxidized nerve tissue is obtained by treating nerve tissue obtained from the spinal cords and brains of bovine, feline, ovine or porcine sources with ozone gas.

6. The topical skin treatment composition of claim 1 wherein said powdery, slightly abrasive material is selected from the group consisting of: an inorganic powder; a metal soap; and an organic powder.

7. The topical skin treatment composition of claim 6 wherein said inorganic powder is selected from the group consisting of: fumed silica, calcium carbonate, calcium acetate, calcium formate, calcium gluconate, calcium lactate, calcium oxalate, calcium phosphate, calcium stannate, magnesium carbonate, zinc carbonate, magnesium aluminum silicate, silica, zinc aluminum silicate, talc, kaolin, cericit, mica, vermiculite, diatomaceous earth, calcium silicate, barium silicate, barium sulfate, hydroxyapatite, zeolite and boran nitride.

8. The topical skin treatment composition of claim 6 wherein said metal soap is selected from the group consisting of aluminum stearate, magnesium stearate and zinc stearate.

9. The topical skin treatment composition of claim 6 wherein said organic powder is selected from the group consisting of: nylon, polyethylene, polytetrafluoroethylene, epoxy, acrylic, microcrystalline cellulose, phenol resin, vinyl resin, vinylidene resin, polyurethane resin, natural rubber, synthetic rubber, chitosan, fibroin, keratin, polyvinylpyrrolidone, polyvinyl alcohol, ethylene oxide polymers, sugars, cellulose, starch, glycogen, carageenan, furcellaren, laminaran sulfate, galactan sulfate, chondroitin sulfate, algin, gum karaya, sodium ethylcellulose sulfate, sodium cellulose acetate sulfate and sodium carboxymethyl cellulose.

10. A topical skin treatment composition comprising:
   a) of from about 12.5 to about 24.5% w/w of unoxidized nerve tissue;
   b) of from about 41 to about 59% w/w of a powdery, slightly abrasive material in finely divided form having an average particle size of from about 0.1 to about 500 μm; wherein said unoxidized nerve tissue and said lightly abrasive material are admixed together; and
   c) a cosmetically/pharmaceutically acceptable carrier, wherein said unoxidized nerve tissue is obtained by heating nerve tissue obtained from the spinal cords and brains of bovine, feline, ovine or porcine sources at a temperature of from about 100° to 165° C. with the exclusion of air.

11. The topical skin treatment composition of claim 10 wherein said unoxidized nerve tissue is obtained by heating nerve tissue obtained from the spinal cords and brains of bovine, feline, ovine or porcine sources at a temperature of from about 60° to 70° C. for about 10 to 20 hours in the presence of:
   water;
   20 to 50% w/w of a polyol selected from the group consisting of sucrose, maltose, lactose, glucose, mannose and galactose; and
   0.01 to 0.5% w/w of a surface active agent selected from the group consisting of polyoxyethylene sorbitan mono- and tri-esters, sodium cholate, sodium taurocholate, sodium deoxycholate and sodium glycocholate.

12. The topical skin treatment composition of claim 10 wherein said unoxidized nerve tissue is obtained by heating nerve tissue obtained from the spinal cords and brains of bovine, feline, ovine or porcine sources at a temperature of from about 60° to 70° C. for about 10 to 20 hours in the presence of:
   water;
   25 to 50% w/w of polyol selected from the group consisting glycerol and polyethylene glycol;
   0.01 to 0.5% w/w of a surface active agent selected from the group consisting of alkyl phenyl polyoxyethylenes, bile salts and benzalkonium chloride.

13. The topical skin treatment composition of claim 10 wherein said unoxidized nerve tissue is obtained by irradiating nerve tissue obtained from the spinal cords and brains of bovine, feline, ovine or porcine sources.

14. The topical skin treatment composition of claim 10 wherein said unoxidized nerve tissue is obtained by treating nerve tissue obtained from the spinal cords and brains of bovine, feline, ovine or porcine sources with ozone gas.

15. The topical skin treatment composition of claim 10 wherein said powdery, slightly abrasive material is selected from the group consisting of: an inorganic powder; a metal soap; and an organic powder.

16. The topical skin treatment composition of claim 15 wherein said inorganic powder is selected from the group consisting of: fumed silica, calcium carbonate, calcium acetate, calcium formate, calcium gluconate, calcium lactate, calcium oxalate, calcium phosphate, calcium stannate, magnesium carbonate, zinc carbonate, magnesium aluminum silicate, silica, zinc aluminum silicate, talc, kaolin, cericit, mica, vermiculite, diatomaceous earth, calcium silicate, barium silicate, barium sulfate, hydroxyapatite, zeolite and boran nitride.

17. The topical skin treatment composition of claim 15 wherein said metal soap is selected from the group consisting of aluminum stearate, magnesium stearate and zinc stearate.

18. The topical skin treatment composition of claim 15 wherein said organic powder is selected from the group consisting of: nylon, polyethylene, polytetrafluoroethylene, epoxy, acrylic, microcrystalline cellulose, phenol resin, vinyl resin, vinylidene resin, polyurethane resin, natural rubber, synthetic rubber, chitosan, fibroin, keratin, polyvinylpyrrolidone, polyvinyl alcohol, ethylene oxide polymers, sugars, cellulose, starch, glycogen, carageenan, furcellaren, laminaran sulfate, galactan sulfate, chondroitin sulfate, algin, gum karaya, sodium ethylcellulose sulfate, sodium cellulose acetate sulfate and sodium carboxymethyl cellulose.

19. The topical skin treatment composition of claim 10 wherein said cosmetically/pharmaceutically acceptable carrier comprises sodium or potassium stearate or sodium potassium palmitate.

20. The topical skin treatment composition of claim 10 wherein said cosmetically/pharmaceutically acceptable carrier is a lotion.

21. The topical skin treatment composition of claim 10 wherein said cosmetically/pharmaceutically acceptable carrier is a cream.

22. The topical skin treatment composition of claim 10 wherein said cosmetically/pharmaceutically acceptable carrier is a suspension.

23. A method of treating human skin to cleanse it by peeling and removing the outermost layer of dead skin, sebum and impurities, said method comprising:
   a) applying by massaging into human skin a composition comprising:
      1) of from about 12.5 to about 24.5% w/w of unoxidized nerve tissue; and
      2) of from about 41 to about 59% w/w of powdery, slightly abrasive material in finely divided form having an average particle size of from about 0.1 to about 500 μm;

said unoxidized nerve tissue and said slightly abrasive material admixed together and lyophilized; and b) flooding said skin with water and rinsing the dead skin, sebum and impurities off the skin;

wherein said unoxidized nerve tissue is obtained by heating nerve tissue obtained from the spinal cords and brains of bovine, feline, ovine or porcine sources at a temperature of from about 100° to 165° C. with the exclusion of air.

24. The method of claim 23 wherein said unoxidized nerve tissue is obtained by heating nerve tissue obtained from the spinal cords and brains of bovine, feline, ovine or porcine sources at a temperature of from about 60° to about 70° C. for about 10 to 20 hours in the presence of:

water;

25 to 50% w/w of a polyol selected from the group consisting of sucrose, maltose, lactose, glucose, mannose and galactose; and 0.01 to 0.5% w/w of a surface active agent selected from the group consisting of polyoxyethylene sorbitan mono- and tri-esters, sodium cholate, sodium taurocholate, sodium deoxycholate and sodium glycocholate.

25. The method of claim 23 wherein said unoxidized nerve tissue is obtained by heating nerve tissue obtained from the spinal cords and brains of bovine, feline, ovine or porcine sources at a temperature of from about 60° to about 70° C. for about 10 to 20 hours in the presence of:

water;

25 to 50% w/w of polyol selected from the group consisting glycerol and polyethylene glycol; and 0.01 to 0.5% w/w of a surface active agent selected from the group consisting of alkyl phenyl polyoxyethylenes, bile salts and benzalkonium chloride.

26. The method of claim 23 wherein said unoxidized nerve tissue is obtained by irradiating nerve tissue obtained from the spinal cords and brains of bovine, feline, ovine or porcine sources.

27. The method of claim 23 wherein said unoxidized nerve tissue is obtained by treating nerve tissue obtained from the spinal cords and brains of bovine, feline, ovine or porcine sources with ozone gas.

28. The method of claim 23 wherein said powdery, slightly abrasive material is selected from the group consisting of: an inorganic powder; a metal soap; and an organic powder.

29. The method of claim 28 wherein said inorganic powder is selected from the group consisting of: fumed silica, calcium carbonate, calcium acetate, calcium formate, calcium gluconate, calcium lactate, calcium oxalate, calcium phosphate, calcium stannate, magnesium carbonate, zinc carbonate, magnesium aluminum silicate, silica, zinc aluminum silicate, talc, kaolin, cericit, mica, vermiculite, diatomaceous earth, calcium silicate, barium silicate, barium sulfate, hydroxyapatite, zeolite and boran nitride.

30. The method of claim 28 wherein said metal soap is selected from the group consisting of aluminum stearate, magnesium stearate and zinc stearate.

31. The method of claim 28 wherein said organic powder is selected from the group consisting of: nylon, polyethylene, polytetrafluoroethylene, epoxy, acrylic, microcrystalline cellulose, phenol resin, vinyl resin, vinylidene resin, polyurethane resin, natural rubber, synthetic rubber, chitosan, fibroin, keratin, polyvinylpyrrolidone, polyvinyl alcohol, ethylene oxide polymers, sugars, cellulose, starch, glycogen, carageenan, furcellaren, laminaran sulfate, galactan sulfate, chondroitin sulfate, pectin., algin, gum karaya, sodium ethylcellulose sulfate, sodium cellulose acetate sulfate and sodium carboxymethyl cellulose.

32. A method of cleansing human skin to remove oily exudate and improve acne conditions comprising:

A) applying by massaging into human skin a composition comprising:

1) of from about 12.5 to about 24.5% w/w of unoxidized nerve tissue;

2) of from about 41 to about 59% w/w of a powdery, slightly abrasive material in finely divided form having an average particle size of from about 0.1 to about 500 μm; said unoxidized nerve tissue and said slightly abrasive material admixed together; and 3) a cosmetically/pharmaceutically acceptable carrier, and B) flooding said skin with water and rinsing off the oily exudate and impurities, wherein said powdery, slightly abrasive material is selected from the group consisting of: an inorganic powder; a metal soap; and an organic powder.

33. The method of claim 32 wherein said unoxidized nerve tissue is obtained by heating nerve tissue obtained from the spinal cords and brains of bovine, feline, ovine or porcine sources at a temperature of from about 60° to 70° C. for about 10 to 20 hours in the presence of:

water;

25 to 50% w/w of polyol selected from the group consisting of sucrose, maltose, lactose, glucose, mannose and galactose; and 0.01 to 0.5% w/w of a surface active agent selected from the group consisting of polyoxyethylene sorbitan mono- and tri-esters, sodium cholate, sodium taurocholate, sodium deoxycholate and sodium glycocholate.

34. The method of claim 32 wherein said unoxidized nerve tissue is obtained by heating nerve tissue obtained from the spinal cords and brains of bovine, feline, ovine or porcine sources at a temperature of from about 60° to about 70° C. for about 10 to 20 hours in the presence of:

water;

25 to 50% w/w of polyol selected from the group consisting glycerol and polyethylene glycol; and 0.01 to 0.5% w/w of a surface active agent selected from the group consisting of alkyl phenyl polyoxyethylenes, bile salts and benzalkonium chloride.

35. The method of claim 32 wherein said unoxidized nerve tissue is obtained by irradiating nerve tissue obtained from the spinal cords and brains of bovine, feline, ovine or porcine sources.

36. The method of claim 32 wherein said unoxidized nerve tissue is obtained by treating nerve tissue obtained from the spinal cords and brains of bovine, feline, ovine or porcine sources with ozone gas.

37. The method of claim 32 wherein said powdery, slightly abrasive material is selected from the group consisting of: an inorganic powder; a metal soap; and an organic powder.

38. The method of claim 37 wherein said inorganic powder is selected from the group consisting of: fumed silica, calcium carbonate, calcium acetate, calcium formate, calcium gluconate, calcium lactate, calcium oxalate, calcium phosphate, calcium stannate, magnesium carbonate, zinc carbonate, magnesium aluminum silicate, silica, zinc aluminum silicate, talc, kaolin, cericit, mica, vermiculite, diatomaceous earth, calcium silicate, barium silicate, barium sulfate, hydroxyapatite, zeolite and boran nitride.

39. The method of claim 37 wherein said metal soap is selected from the group consisting of aluminum stearate, magnesium stearate and zinc stearate.

40. The method of claim 37 wherein said organic powder is selected from the group consisting of: nylon, polyethylene, polytetrafluoroethylene, epoxy, acrylic, microcrystalline cellulose, phenol resin, vinyl resin, vinylidene resin, polyurethane resin, natural rubber, synthetic rubber, chitosan, fibroin, keratin, polyvinylpyrrolidone, polyvinyl alcohol, ethylene oxide polymers, sugars, cellulose, starch, glycogen, carageenan, furcellaren, laminaran sulfate, galactan sulfate, chondroitin sulfate, pectin., algin, gum karaya, sodium ethylcellulose sulfate, sodium cellulose acetate sulfate and sodium carboxymethyl cellulose.

41. The method of claim 32 wherein said cosmetically/pharmaceutically acceptable carrier is a lotion.

42. The method of claim 32 wherein said cosmetically/pharmaceutically acceptable carrier is a cream.

43. The method of claim 32 wherein said cosmetically/pharmaceutically acceptable carrier is a suspension.

* * * * *